United States Patent

Muschler et al.

[11] Patent Number: 5,429,638
[45] Date of Patent: Jul. 4, 1995

[54] BONE TRANSPORT AND LENGTHENING SYSTEM

[75] Inventors: George F. Muschler, Cleveland Hts.; Helmuth Kotschi, Strongsville, both of Ohio

[73] Assignee: The Cleveland Clinic Foundation, Cleveland, Ohio

[21] Appl. No.: 17,622

[22] Filed: Feb. 12, 1993

[51] Int. Cl.⁶ .................................... A61B 17/56
[52] U.S. Cl. ........................... 606/60; 606/62
[58] Field of Search ..................... 606/62–68, 606/77, 78, 86, 87, 88

[56] References Cited

U.S. PATENT DOCUMENTS

| | | | |
|---|---|---|---|
| 4,157,715 | 6/1979 | Westerhoff | 606/60 |
| 4,576,158 | 3/1986 | Boland | 606/102 |
| 4,846,162 | 7/1989 | Moehring | 606/67 |
| 4,877,019 | 10/1989 | Vives | 606/64 |
| 5,002,543 | 3/1991 | Bradshaw | 606/62 |
| 5,034,012 | 7/1991 | Frigg | 606/62 |
| 5,152,794 | 10/1992 | Davidson | 606/76 |
| 5,242,448 | 9/1993 | Pettine | 606/102 |

Primary Examiner—Michael A. Brown
Attorney, Agent, or Firm—Pravel, Hewitt, Kimball & Krieger

[57] ABSTRACT

A traction cable device is disclosed for bone lengthening and for bone segment transport. The apparatus features a flexible cable contained within a flexible sheath. Bone transport continues after osteotomy and until the bone segment contacts the proximal femur. The in vivo force exerted by the cable can be measured as well as translation of the cable relative to its sheath.

37 Claims, 2 Drawing Sheets

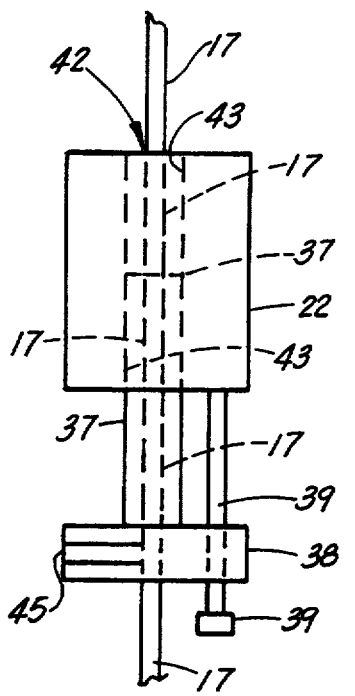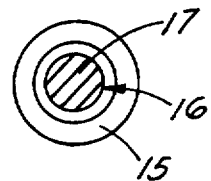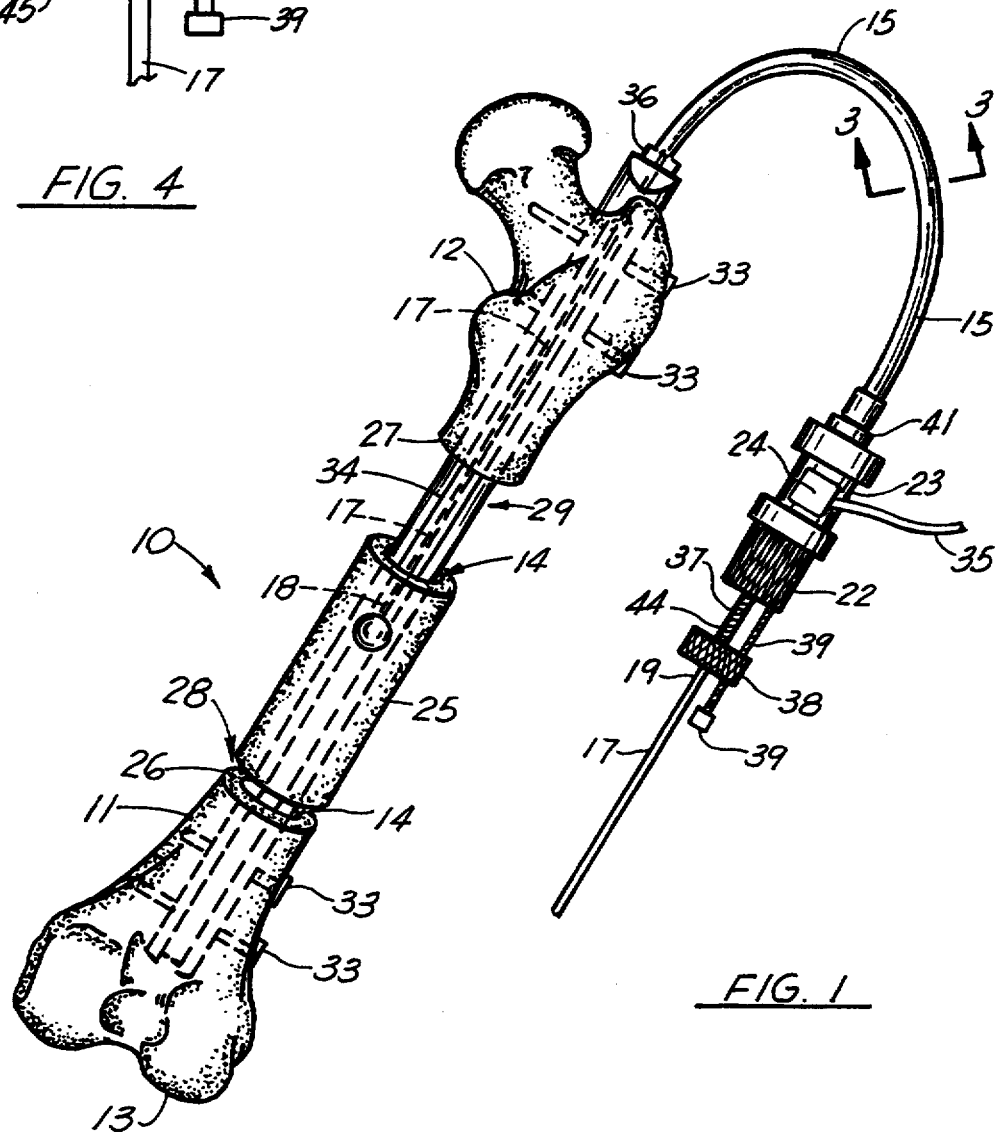

BONE TRANSPORT AND LENGTHENING SYSTEM

BACKGROUND OF THE INVENTION

1. Field of the Invention

The present invention relates to in vivo bone transport and lengthening. More particularly, the present invention relates to a flexible cable drive system for in vivo bone transport and lengthening and force transmission to bone tissue that allows clinically convenient placement of a driver and exit portal, and which does not significantly hinder the patient's normal activities.

2. General Background

Intercalary defects in long bones may occur as a result of trauma or after the resection of tumors or infection. With appropriate mechanical fixation, these defects may be managed by autogenous bone grafting, segmental allograft reconstruction, or reconstruction using endoprostheses. Autogenous bone grafting has the disadvantage of donor site morbidity including pain, increased blood loss, and surgical scarring. Furthermore, in the case of large defects it may be difficult or impossible to obtain an optimal volume of autogenous bone. While allografting eliminates the problem of adequate quantity, the incidence of complications such as infection, fracture, and non-union is increased. The risk of exposure to HIV or hepatitis is another concern.

In 1954 Ilizarov reported that mature bone can be elongated by gradual distraction of a fracture callus and called this process distraction osteogenesis. The application of this technique in the form of bone segment transport can obviate the need for open bone grafting in many large diaphyseal defects. However, transfixing wires used in this technique can cause significant complications including wire site infection, pain, and restricted joint motion due to the transfixation of tendons and muscles. These complications are particularly relevant when the Ilizarov device is applied to the femur.

In 1990 Brunner reported that distraction osteogenesis was achievable using intramedullary fixation in sheep tibiae. Brunner's method still relied on the use of an external fixator to provide the force necessary for bone transport. Brunner's work implied that transfixing wires used for internal fixation could potentially be eliminated.

Betz described the use of a telescoping intramedullary rod for distraction osteogenesis. With the Betz device, the patient apparently turned a small knob that protruded from the patient's hip in order to telescopically move the parts relative to one another.

Various patents have issued for implantable distractor devices. Further, certain devices have been published in the literature as published patent applications for example.

An example of a medullary nail is seen in PCT Application No. WO 91/00065 naming Rainer Baumgart and Augustin Betz as applicants. The Betz device describes an intramedullary nail that has a cavity in which an inner part can slide longitudinally without being able to rotate. The wall of the medullary nail which forms the cavity is traversed on both sides by an elongated hole in the region of the driving-in end. At least one fastening hole aligned flush with the elongated hole is provided in the inner part. When the connecting screws are driven into the spaced fastening holes an osteotomy is located between the connecting screws, the edges of the osteotomy are moved apart as the inner part slides longitudinally, and the slowly widening gap between the edges of the osteotomy becomes filled with bone tissue.

An extension apparatus, especially for osteotomic surgery is the subject of U.S. Pat. No. 3,976,060 issued to Hildebrandt et al. The Hildebrandt patent describes a bone extension device that is movably supported in an elongated, slender housing. The extension device includes an extension member movably extending out of a housing. A drive is supported within the housing and operatively connected to the extension device. A drive is energized through a source of power which may be either located in the housing itself or it may be an external power source such as a magnetic field. The power source is operatively connected to the drive. A control is supported within the housing to operate the drive through the power source for moving the extension member. A seal is provided to seal the housing so as to provide a surgically implantable structural unit. The power source can be an electric motor and powered by a battery. Reduction gears are disclosed as rotating a threaded spindle which operates a push rod.

U.S. Pat. No. 4,1577,715 entitled "Intracorporal Drive to Produce a Continuous Traction or Pressure and Method of Operating Same" was issued to Erhardt Westerhoff. The drive provides an extension unit for extension osteotomy and for a compression unit for pressure osteosynthesis, wherein the driving power is generated by the osmotic pressure between two differentially concentrated solutions separated from each other by a semipermeable diaphragm or membrane. The solution of low concentration can also be substituted by pure solvent.

The Grammont et al. U.S. Pat. No. 5,074,882 provides a device that includes a nail for gradually lengthening long bones. The apparatus includes outer and inner sliding tubes connected with a double ratchet mechanism. The nail is fixed by its two extremities in the bone and the device is entirely included within the concerned bone, being lengthened post-operatively by maneuvers applied to the patient's limb. Rotation of a distal part of the limb with respect to the proximal part of the limb allows rotation of the ratchet mechanism with lengthening of the device in one direction, and keeping of the gained length in the other direction while returning the neutral axis of the rotation of the device, thereby featuring a dynamization system, and a system, to limit the range of rotation of the device.

The linear implantable distractors of the prior art suffer because of a failure to afford an easy way of operating such an implantable distraction apparatus, with improved patient comfort, and without bacteriological infiltration.

Various devices have been patented for distractors that are placed externally of the patient's limb. These are referred to often as "Ilizarov-type" distractors, after the Russian inventor Gavriil Ilizarov. As an example, U.S. Pat. No. 4,615,338 entitled "Automatic Compression-Distraction Apparatus" names Gavriil Ilizarov and others as inventors. The '338 patent relates to a drive of a compression-distraction apparatus, comprising a lead screw whose thread is mated with an opening of a ratchet wheel placed in a housing, a pawl interacting with teeth of the wheel and connected to a load bearing element manufactured from an alloy possession plastic memory. The load bearing element has a rectilinear shape and is essentially a tie rod whose one end is rigidly secured to the housing while the other end is coupled to a resilient member and the pawl, with the load bearing element being further provided with an electric heater connected to the housing. Another external compression distraction apparatus is the subject of U.S. Pat. No. 4,973,331 issued to Pursley et al. and entitled "Automatic Compression-Distraction, Torsion Method and Apparatus".

SUMMARY OF THE INVENTION

The present invention solves these prior art problems and shortcomings by providing a surgically implantable traction cable apparatus for in vivo bone transplant, bone lengthening or force transmission to a bone segment. The apparatus includes a flexible cable having a first end portion that can be attached to a bone segment to which force is to be applied. An implantable flexible, non-compressible sheath with a bore is provided for supporting the cable and holding it within the bore, and through which a counter-compression force can be transmitted to the bone. Force can be applied to the bone segment such as by pulling the cable through the sheath.

The apparatus can include rod that is adapted to be surgically implanted into the intramedullary canal of the patient's bone. A sheath can engage an end portion of the rod during use. The rod carries openings at its end portions for receiving bone screws so that the rod can be affixed at its end portions to the patient's bone tissue.

The barrier sheath excludes bacteria or debris from the apparatus when it extends outside of the patient. Application of the barrier sheath can also include a layer to enhance fibrous tissue ingrowth or sealing of the tissue interface where the implant enters the body.

The sheath preferably provides a cell ingrowth substrate thereon so that the patient's skin adheres to the cell ingrowth substrate where the sheath exits the patient's body.

The present invention provides a method of maintaining sterility of a bone transport or bone lengthening apparatus which passes from the inside of a patient's bone to the outside and is intended to be maintained in a sterile condition for a period of time. The apparatus includes an impermeable sterile membrane (barrier) which completely surrounds the operating portion of the device protruding from the skin.

The inside of the membrane (barrier) is sufficiently large to allow necessary mechanical manipulation of the device within the membrane.

The membrane is durable enough to allow manipulation of the protected device without compromise of the membranes integrity.

The membrane covering the device extend with the device into the patient's body where it may be fixed to a portion of the device or to the patient's tissue to maintain it's position.

The membrane surface may be modified or coated in the region where the device and membrane enter the patient's body to promote adherence and/or ingrowth of tissue for the purpose of accomplishing a biologic seal preventing the invasion of bacteria or debris along the membrane-tissue interface.

The present invention thus provides a surgically implantable cable apparatus for the transmission of force to bone or a bone segment, and from outside the patient to a site inside the patient. Force such as traction can be applied to the bone segment by pulling the cable through the sheath and along a desired path. The path can be generally aligned with the intramedullary canal of the patient's bone. The method of the present invention allows a single cable to be used rather than multiple wires. The method utilizes a flexible cable which slides inside a flexible and non-compressible sheath.

Flexibility reduces the morbidity of the device by allowing it to flex freely with and within surrounding tissue. The device therefore does not limit movement of muscles or joints even during the time when force is being applied through it.

With the method of the present invention, the application of in vivo force can be to move one bone fragment with respect to another (push or pull, together or apart), to squeeze or hold bones or bone fragments together (internal fixation), or to hold bone fragments apart.

The method of the present invention can include measurement of the in vivo force being applied to the cable. The system of the present invention can include a measurement of the linear distance that the cable is pulled through the sheath.

The flexible cable may be monofilament or polyfilament in construction.

If the device extends outside of the patient's body, the site of exit of the device can be selected to be convenient for patient manipulation and maintenance. (For example if force is being applied to the femur the exit site could be selected on the patient's ipsilateral anterior thigh or on the patient's abdomen in an accessible location.)

The traction cable sheath of the present invention can be assembled for use in several ways:

a) The cable and sheath can be passed through appropriate tissues in relatively opposite directions articulating the cable through the sheath;

b) The cable and sheath can be advanced together or separately in the same direction with the cable advanced beyond the sheath and affixed to the appropriate point at which force is to be applied;

c) The cable and sheath can be advanced in the same direction and then affixed to appropriate portions of an implant or bone to which force is to be applied;

d) The cable and sheath can be advanced with the cable and/or sheath prefixed or assembled as part of an implant.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein:

FIG. 1 is a perspective schematic view of the preferred embodiment of the apparatus of the present invention;

FIG. 3 is a sectional view taken along lines 3—3 of FIG. 1; and

FIG. 4 is a fragmentary view of the preferred embodiment of the apparatus of the present invention.

DETAILED DESCRIPTION OF THE PREFERRED EMBODIMENT

Figure 2:
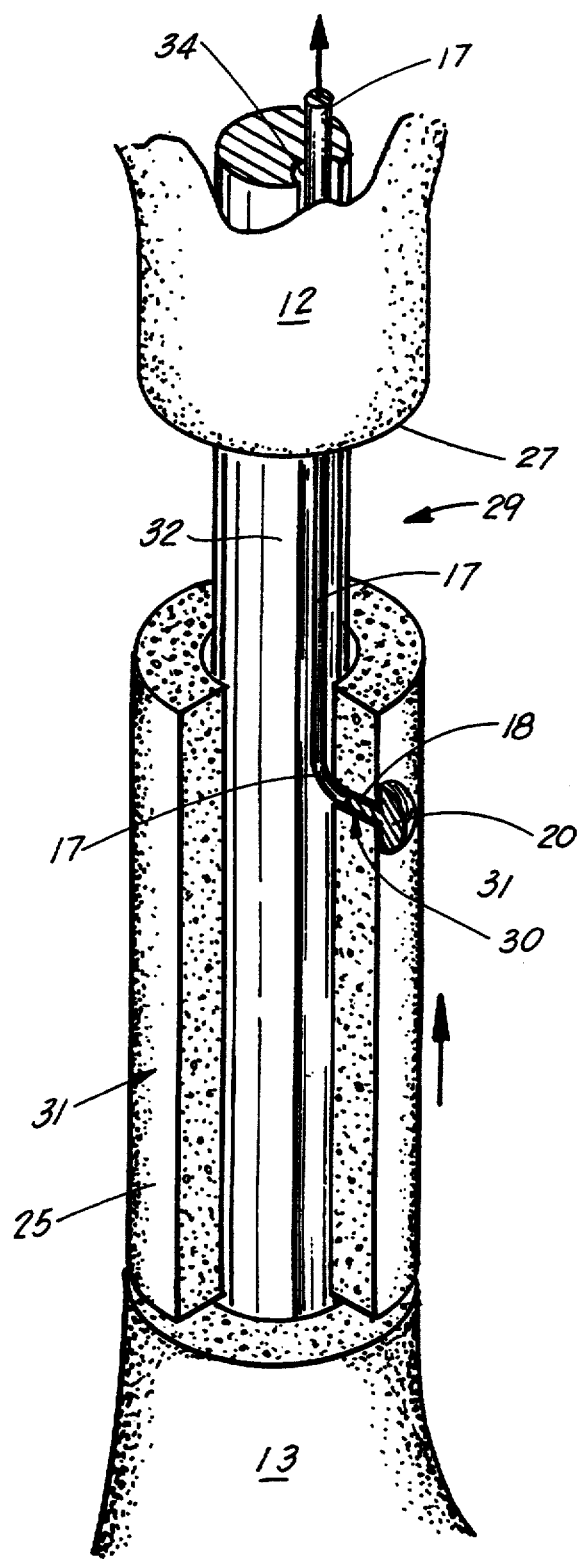
FIG. 2 is a perspective partially cut away fragmentary view of the preferred embodiment of the apparatus of the present invention.

FIGS. 1 and 2 illustrate generally the preferred embodiment of the apparatus of the present invention designated generally by the numeral 10. Bone transport and lengthening apparatus 10 can be seen in FIG. 1 in use with a patient's femur designated by the numeral 11. The femur 11 is exemplary of a bone that can be used with the method and apparatus of the present invention. The femur 11 includes a proximal end portion 12, a distal end portion 13, and intramedullary canal 14.

The apparatus 10 includes a flexible outer cable or sheath 15 of a preferably non-compressible material such as a coil spring cable of stainless steel polymeric, or like material. Flexible sheath 15 has an internal bore 16 for accepting flexible cable 17. The flexible cable 17 can be a monofilament cable, or a multifilament cable. The cable 17 can be metallic or polymeric for example.

Cable 17 includes a distal end portion 18 and a proximal end portion 19. The distal end portion 18 carries button 20 or other means for attaching the distal end 18 of cable 17 to bone segment 25. In FIGS. 1 and 2, bone segment 25 is formed by cuts 26, 27 defining gaps 28, 29. The larger gap 29 represents an area where a large bone segment was excised or was absent from the proximal end portion 12 of femur 11.

The cut 26 in the small gap 28 represents an osteotomy that was made a selected distance above the distal end 13 of femur 11. Following the osteotomy, the bone segment 25 is formed for bone transport. Cable 17 is attached to bone segment 25 using button 20 for example. The segment 25 can be advanced a desired distance per unit time by pulling the cable 17. A hole 30 is formed (such as by drilling) in the bone segment 25 for attachment of the cable 17 to the bone segment 25. The cable is advanced through the hole 30 until the button 20 contacts the outer surface 31 of bone segment 25 as shown in FIG. 2. The free bone segment 25 can then be transported proximally along rod 32 which is implanted in the patient's intramedullary canal.

The intramedullary canal is initially prepared proximally and distally (such as by reaming with a reamer) to a desired diameter so that rod 32 (for example stainless steel) can be advanced from the proximal 12 to the distal 13 end portions of femur 11 as shown in FIG. 1. The rod 32 is held in position for example using a plurality of bone screws 33. Each end portion of rod 32 includes multiple transverse openings for accepting bone screws 33 therethrough. The rod 32 can have a longitudinally extending slot 34. Cable 17 tracks the slot 34 during bone transport as shown in FIGS. 1 and 2.

Transportation of the bone segment 25 can begin within about one week after the osteotomy for example and can continue at a desired rate (one millimeter per day for example) and for a number of days until docking occurs. Docking occurs when the bone segment 25 eventually contacts the cut 27 at the proximal femur 11.

Tension on the cable 17 can be measured before and after each distraction with load cell 23 that carries strain gauge 24. The proximal end 19 of wire 17 can be measured to determine translation of cable 17 with respect to sheath 15. An instrumentation wire 35 can communicate the load information from strain gauge 24 to a suitable display such as a commercially available load cell monitor. The sheath 15 affixes to rod 32 at 36. This connection 36 allows traction force to be transmitted from the proximal end 19 of cable 17 to bone segment 25, countered by a compression force at connection 36.

Force can be applied to cable 17 using force transmitting knob 22 (FIGS. 1 and 4) that rotates upon externally threaded tube 37. Knob 22 provides an internally threaded bore 42 for receiving the threaded hollowed tube 37. The hollowed tube 37 has a central longitudinally extending and open ended bore that allows passage of cable 17 therethrough (FIG. 4). The external threads 44 of tube 37 correspond to and engage the internal threads 43 of the internally threaded bore 42. Cable 17 is clamped to the non-rotating knob 38 using set screw 45 for example. During use, the rotating knob 22 can be rotated. The knob 22 includes internal threads 43 that accept the threads 44 of threaded tube 37. In this manner, rotation of the knob 22 causes a translation of the threaded tube member 37 upwardly or downwardly, depending upon the direction of rotation of knob 22. The cable is clamped with set screw 45, and travels with the knob 38.

As the knob 22 is rotated, the cable 17 is pulled, and the bone segment 25 advances. In this manner, a bone segment could be pushed as well by using the compression force applied by sheath 15. After each distraction, set screw 39 can be tightened to rigidify a rotation of knob 23 with respect to knob 38. The set screw 39 is threadably attached to knob 38, occupying a threaded bore that extends through the knob 38, generally parallel to wire 17. At knob 22, the set screw simply frictionally engages the knob 22 when the set screw 39 is tightened. Each time a new distraction is required, the set screw 39 is loosened, and knob 23 rotated to create the desired movement of cable 17. The load cell 23 is in compression during traction, being compressed between the rotating knob 23 and flanged end 40 of sheath 15. Load cell 23 carries strain gauge 24 that can be interfaced with an indicator, printout or like using instrumentation wire 35.

The following table lists the part numbers and part descriptions as used herein and in the drawings attached hereto.

| Part Number | PARTS LIST Description |
|---|---|
| 10 | bone transport lengthening apparatus |
| 11 | femur |
| 12 | proximal end |
| 13 | distal end |
| 14 | intramedullary canal |
| 15 | flexible sheath |
| 16 | bore |
| 17 | flexible cable |
| 18 | distal end cable |
| 19 | proximal end cable |
| 20 | button |
| 21 | attachment opening |
| 22 | force transmitting knob |
| 23 | load cell |
| 24 | strain gauge |
| 25 | bone segment |
| 26 | cut |
| 27 | cut |
| 28 | gap |
| 29 | gap |
| 30 | hole |
| 31 | outer surface |
| 32 | rod |
| 33 | bone screws |
| 34 | slot |
| 35 | wire |
| 36 | connection |
| 37 | threaded tube |
| 38 | knob |
| 39 | set screw |
| 40 | opening |
| 41 | flanged end |
| 42 | intramedullary threaded bore |
| 43 | internal threads |
| 44 | external threads |

| PARTS LIST | |
|---|---|
| Part Number | Description |
| 45 | set screw |

EXAMPLE I

Five skeletally mature, male mongrel dogs (25 kg) were used in Example 1. A two centimeter (2 cm) bone segment was excised from the proximal shaft of the left femur. The intramedullary canal was reamed proximally and distally with a straight drill to a diameter of ten millimeters (10 mm), a fifteen centimeter (15 cm) long custom stainless steel rod was advanced proximal to distal. An osteotomy was then made six centimeters (6 cm) above the knee joint, crating a four centimeter (4 cm) long vascularized bone segment for transport. A braided stainless steel cable was attached to the free bone segment through a drill hole and was advanced to the end of the rod and through a coiled cable sheath passed under the skin exiting the dorsal thoracic area.

The free bone segment was transported proximally along the rod by pulling the cable through the cable sheath. Transportation began one week after osteotomy and continued at a rate of one millimeter (1 mm) per day for twenty (20) days or until docking occurred. X rays were taken weekly. Tension on the cable was measured before and after each distraction with a strain-gauged spool placed between the cable and the cable sheath. In these animals the maximum force reached over one hundred sixty (160) Newtons before docking or consolidation occurred. The stiffness increased during distraction from minimum to over sixty (60) N/mm at the end of distraction.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A surgically implantable cable apparatus for in vivo bone transport of a first bone segment that is spaced from a second bone segment comprising:
   a) a flexible cable having a first end portion with means for attaching the cable to the first bone segment to which force is to be applied;
   b) an implantable prosthetic flexible, non-compressible sheath with a bore for accepting the cable, and through which a counter-compression force can be transmitted to the bone;
   c) means for attaching the sheath to the second bone segment; and
   d) means for applying force to the first bone segment by pulling the cable through the sheath to move the first and second segments relative to each other over a period of time after surgical implantation when the cable is manipulated to move through the sheath.

2. The surgically implantable cable apparatus of claim 1 wherein the cable is positioned longitudinally during use, generally parallel to the longitudinal axis of the intramedullary canal of the patient's bone.

3. The surgically implantable cable apparatus of claim 1 wherein the sheath carries a cell ingrowth substrate.

4. The surgically implantable cable apparatus of claim 1 wherein the sheath is covered with a barrier layer that prevents pathogen travel to the sheath and flexible cable.

5. The surgically implantable cable apparatus of claim 4 wherein the barrier layer carries a cell ingrowth substrate.

6. A surgically implantable cable apparatus for in vivo bone transport of a first bone segment that is spaced from a second bone segment comprising:
   a) a flexible cable having a first end portion with means for attaching the cable to the first bone segment to which force is to be applied;
   b) an implantable prosthetic flexible, non-compressible sheath with a bore for accepting the cable and through which a counter-compression force can be transmitted to the bone;
   c) means for attaching the sheath to the second bone segment;
   d) Wherein force can be applied to the first bone segment by pulling the cable through the sheath to move the first and second segments relative to each other when the cable is manipulated to move through the sheath; and
   e) means for measuring the force applied by the apparatus.

7. A surgically implantable cable apparatus for in vivo bone transport of a first bone segment that is spaced from a second bone segment comprising:
   a) a flexible cable having a first end portion with means for attaching the cable to the first bone segment to which force is to be applied;
   b) an implantable prosthetic flexible, non-compressible sheath with a bore for accepting the cable, and through which a counter-compression force can be transmitted to the bone;
   c) means for attaching the sheath to the second bone segment;
   d) wherein force can be applied to the first bone segment by pulling the cable through the sheath to move the first and second segments relative to each other when the cable is manipulated to move through the sheath; and
   e) means for measuring the translation of the cable within the sheath.

8. A surgically implantable cable apparatus for in vivo bone transport of a first bone segment that is spaced from a second bone segment comprising:
   a) a flexible cable having a first end portion with means for attaching the cable to the first bone segment to which force is to be applied;
   b) an implantable prosthetic flexible, non-compressible sheath with a bore for accepting the cable, and through which a counter-compression force can be transmitted to the bone;
   c) means for attaching the sheath to the second bone segment;
   d) means for applying force to the first bone segment by pulling the cable through the sheath to move the first and second segments relative to each other when the cable is manipulated to move through the sheath; and
   e) a device adapted to be surgically implanted and affixed to the patient's bone, the device having portions to accept the sheath and cable.

9. A surgically implantable cable apparatus for in vivo bone transport of a first bone segment that is spaced from a second bone segment comprising:

a) a flexible cable having a first end portion with means for attaching the cable to the first bone segment to which force is to be applied;

b) an implantable prosthetic flexible, non-compressible sheath with a bore for accepting the cable, and through which a counter-compression force can be transmitted to the bone;

c) means for attaching the sheath to the second bone segment;

d) means for applying force to the first bone segment by pulling the cable through the sheath to move the first and second segments relative to each other when the cable is manipulated to move through the sheath; and e) means at its end portions for affixing the device to the patient's bone tissue.

10. A surgically implantable cable apparatus for in vivo bone transport of a first bone segment that is spaced from a second bone segment comprising:

a) a flexible cable having a first end portion with means for attaching the cable to a first bone segment to which traction is to be applied;

b) an implantable prosthetic flexible, sheath with a bore for accepting the cable, and through which a counter-compression force can be transmitted to the bone;

c) means for attaching the sheath to the second bone segment; and d) means for applying force to the first bone segment by pulling the cable through the sheath to gradually, incrementally move the first and second bone segments away from each other over a period of time after surgery when the cable is pulled through the sheath along a path that is generally aligned with the intramedullary canal of the patient's bone.

11. The surgically implantable cable apparatus of claim 10 further comprising means for measuring the force applied by the apparatus.

12. The surgically implantable cable apparatus of claim 10 further comprising an intramedullary rod adapted to be surgically implanted into the intramedullary canal of a patient's bone, the rod having end portions to accept the sheath and cable during use.

13. The surgically implantable cable apparatus of claim 12 wherein the rod carries means at the rod end portions for affixing the rod to the patient's bone tissue.

14. The surgically implantable cable apparatus of claim 10 wherein the cable is positioned longitudinally during use, generally parallel to the longitudinal axis of the intramedullary canal of the patient's bone.

15. The surgically implantable cable apparatus of claim 10 wherein the sheath carries a cell ingrowth substrate.

16. The surgically implantable cable apparatus of claim 10 wherein the sheath is covered with a barrier layer that prevents pathogen travel to the sheath and flexible cable.

17. The surgically implantable cable apparatus of claim 16 wherein the barrier layer carries a cell ingrowth substrate.

18. A surgically implantable apparatus for in vivo bone transport of a first bone segment that is spaced from a second bone segment comprising:

a) a flexible cable having a first end portion with means for attaching the cable to a first bone segment to which traction is to be applied:

b) an implantable prosthetic flexible, sheath with a bore for accepting the cable, and through which a counter-compression force can be transmitted to the bone;

c) means for attaching the sheath to the second bone segment;

d) wherein force can be applied to the first bone segment by pulling the cable through the sheath to move the first and second segments away from each other when the cable is pulled through the sheath along a path that is generally aligned with the intramedullary canal of the patient's bone; and e) means for measuring the translation of the cable within the sheath.

19. Apparatus for in vivo lengthening the bone of a patient, comprising:

a) a flexible implant sheath that is surgically implantable and fixed to a patient's bone to be lengthened;

b) flexible operating cable means connected to and extending from the flexible implant sheath and including a remote end portion that is positioned a distance from the patient's bone for mechanically transmitting tensile force to the bone using a force that is applied to said remote end portion of the cable means;

c) means for affixing the implant sheath to the bone; and d) the flexible implant sheath and cable means defining means for incrementally advancing at least a portion of the cable means into the bone over a period of time after the surgical implantation.

20. The bone lengthening apparatus of claim 19 wherein the cable includes an inner cable and an outer sheath.

21. The bone lengthening apparatus of claim 19 wherein the implant includes moving and fixed portions, and the flexible cable means includes means for extending the moving and fixed portions.

22. The bone lengthening apparatus of claim 19 further comprising means for measuring in vivo distraction force applied to the prosthesis.

23. The bone lengthening apparatus of claim 19 wherein the cable means includes a traction cable that can mechanically transmit force along its length.

24. The bone lengthening apparatus of claim 19 wherein the flexible cable means includes a traction cable that has a first end portion that affixes to the prosthesis implanted in the patient's intramedullary canal, and a second end portion that extends away from the bone during use, and the second end portion has means for transmitting a traction force to the bone via the cable.

25. A method for lengthening a patient's bone, comprising the steps of:

a) affixing an implant to the bone;

b) severing the selected bone with a cut that defines a gap;

c) affixing the implant to the bone tissue at separate positions on opposite sides of the gap;

d) gradually moving at least a portion of the implant a selected dimension per unit of time; and e) wherein in step "d" a flexible force transmitting member extends from the implant to a remote site where force is applied thereto.

26. The method of claim 25 wherein the remote site is externally of the patient's body.

27. The method of claim 26 further comprising the step of forming a tissue ingrowth site at the patient's skin surface with the outer surface of the flexible force transmitting member.

28. The method of claim 26 or 27 further comprising the step of flexing the force transmitting member so that the force transmitting member exits the patient's body at a desired and clinically convenient site as selected by the patient's surgeon.

29. The method of claim 25 wherein in step "a" the implant is place in the intramedullary canal of the patient's bone.

30. The method of claim 25 wherein the implant includes a rod member.

31. The method of claim 25 wherein the force transmitting member is flexible along at least a portion of its length.

32. The method of claim 25 further comprising the step of rotating a force transmitting member to move at least a portion of the prosthesis.

33. The method of claim 25 further comprising the step of sealing the flexible cable to prevent the travel of microorganisms thereto.

34. The method of claim 25 wherein in steps "d" and "e" a surgeon manually extends the prosthesis by manipulating the flexible force transmitting member.

35. The method of claim 25 wherein the flexible force transmitting member includes flexible cable contained within a flexible sheath.

36. The method of claim 35 wherein in step "b" the prosthesis is a telescoping rod, and the flexible cable communicates with the rod.

37. The method of claim 36 wherein rotation of the flexible cable extends the telescoping rod.

* * * * *